United States Patent
Kumosani et al.

(10) Patent No.: US 10,154,958 B1
(45) Date of Patent: Dec. 18, 2018

(54) COMPOSITION CONTAINING ESSENTIAL OILS AND PLANT EXTRACTS FOR TREATING VAGINAL INFECTION AND INFLAMMATION

(71) Applicant: King Abdulaziz University, Jeddah (SA)

(72) Inventors: Taha Abdullah Kumosani, Jeddah (SA); Elie Kamil Barbour, Jeddah (SA); Werner Krull, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 15/654,765

(22) Filed: Jul. 20, 2017

(51) Int. Cl.
| | |
|---|---|
| *A61K 9/08* | (2006.01) |
| *A61K 36/28* | (2006.01) |
| *A61K 36/537* | (2006.01) |
| *A61K 45/06* | (2006.01) |
| *A61K 31/765* | (2006.01) |
| *A61K 9/00* | (2006.01) |

(52) U.S. Cl.
CPC .......... *A61K 9/0034* (2013.01); *A61K 31/765* (2013.01); *A61K 36/28* (2013.01); *A61K 36/537* (2013.01); *A61K 45/06* (2013.01)

(58) Field of Classification Search
None
See application file for complete search history.

(56) References Cited

U.S. PATENT DOCUMENTS

2015/0098989 A1    4/2015   Ferrer Montiel et al.

FOREIGN PATENT DOCUMENTS

| JP | 2003-81840 | 3/2003 |
| WO | 2011/002929 | 1/2011 |
| WO | 2013/139965 | 9/2013 |

OTHER PUBLICATIONS

Rigane et al., "Investigation into the biological activities and chemical composition of *Calendula officinalis* L. growing in Tunisia", International Food Research Journal, 2013, vol. 20(6), pp. 3001-3007.*

Honig et al., "From bench to clinic and back: Perspective on the 1st IQPC Translational Research conference", Journal of Translational Medicine, 2004, vol. 2(44).*

Vincenzo De Leo et al., "Pharmaceutical, Microbiological and Clinical Activity of Feminine Intimate Cleansers Based on Plant Extracts Active Principles (Saugella Line)," Women's Health Care, 2015, vol. 4, No. 4, 8 Pages.

Soin et Nature, "Intimate hygiene gel saugella girl 200ml," 4 Pages. https://www.soin-et-nature.com/en/vaginal-gel/6268-intimate-hygiene-gel-saugella-girl-200ml.html.

* cited by examiner

*Primary Examiner* — Savitha M Rao
*Assistant Examiner* — Gregg Polansky
(74) *Attorney, Agent, or Firm* — Oblon, McClelland, Maier & Neustadt, L.L.P.

(57) ABSTRACT

A composition containing essential oils of two different species of *Origanum*, emulsified in water extracts of four herbs. The composition may be useful for prevention and/or treating major infections by pathogens such as *Trichomonas vaginalis, Gardnerella vaginalis,* and *Candida albicans.* When the composition is administered as a vaginal douche, rapid restoration of *lactobacillus* colony may occur after the administration.

12 Claims, No Drawings

COMPOSITION CONTAINING ESSENTIAL OILS AND PLANT EXTRACTS FOR TREATING VAGINAL INFECTION AND INFLAMMATION

BACKGROUND

Technical Field

The disclosure relates to a composition containing essential oils and plant extracts for treating, vaginal infection and/or inflammation. The composition may also enable the reestablishment of the normal microbiota shortly after the administration of the composition.

Description of Related Art

There is literature reporting synthetic chemical-based douches for vaginal hygiene.

U.S. Pat. No. 5,292,532, incorporated herein by reference in its entirety, describes an aqueous antibacterial and antifungal vaginal douche composed of adherent gum, a penetrant, miconazole, and nystatin.

U.S. Pat. No. 5,466,463, incorporated herein by reference in its entirety, describes a douche composition based on benzalkonium chloride, cetylpyridinium chloride, chlorhexidine, gluconate, povidone iodine, imidiazolidinyl urea, or diazolidinyl urea, and a viable colony of micro-encapsulated *lactobacilli* bacteria.

U.S. Pat. No. 5,466,680, incorporated herein by reference in its entirety, describes a composition for providing energy and ions for enhancing the function of mucosal white blood cells to defend against infections.

U.S. Pat. No. 5,741,525, incorporated herein by reference in its entirety, describes a composition of a vaginal gel containing a water-soluble bio-adhesive polymer, a peroxide source, and a pH buffer to prevent, treat, and mitigate vaginal diseases.

U.S. Pat. No. 5,778,886, incorporated herein by-reference in its entirety, describes a composition of vaginal douche containing spermicidal agent (nonoxynol-9) and a peroxugen, preferably hydrogen peroxide.

U.S. Pat. No. 7,687,078, incorporated herein by reference in its entirety, describes a composition containing magnesium and alkali salts at an acidic pH for treating anal and vaginal inflammations while maintaining normal microbiota.

WIPO Pat. No. 2004045572, incorporated herein by reference in its entirety, describes a composition containing an antimicrobial compound, an essential oil, and a carrier for treatment of mucosal membranes and infected skin.

However, there is an emergence of vaginal pathogens resistant to the commonly used active ingredients (especially chlorhexidine) in vaginal douches. As such, it is an objective of the present disclosure to prepare a composition with plant extracts for treating vaginal infection and/or inflammation without adversely affecting the normal vaginal microbiota.

SUMMARY OF THE INVENTION

A first aspect of the disclosure relates to a c position, comprising: (i) 0.01-10 g/L of an essential oil extracted from at least one species of *Origanum*; (ii) 100-500 g/L of an aqueous extract of at least one species of *Calendula*; (iii) 100-500 g/L of an aqueous extract of at least one species of *Matricarta*; (iv) 100-500 g/L of an aqueous extract of at least one species of *Malva*; (v) 100-500 g/L of an aqueous extract of at least one species of *Salvia*; and(vi) 1-100 g/L polyoxyethylene sorbitan, each based on a total volume of the composition, where a pH of the composition is in a range of 4-5.5, and the composition is substantially free of a $C_1$-$C_6$ aliphatic alcohol, an aromatic alcohol, and a $C_3$-$C_{25}$ diol.

In one embodiment, the at least one species of *Origanum* is selected from the group consisting of *Origanum acutidens*, *Origanum akhdarense*, *Origanum amanum*, *Origanum bargyli*, *Origanum bilgeri*, *Origanum boissieri*, *Origanum calcaratum*, *Origanum compactum*, *Origanum cordifolium*, *Origanum cyrenaicum*, *Origanum dayi*, *Origanum dictamnus*, *Origanum ehrenbergii*, *Origanum elongatum*, *Origanum floribundum*, *Origanum haussknechtii*, *Origanum husnucan-baseri*, *Origanum hypericifolium*, *Origanum isthmicum*, *Origanum jordanicum*, *Origanum laevigatum*, *Origanum leptocladum*, *Origanum libanoticum*, *Origanum majorana*, *Origanum microphyllum*, *Origanum minutiflorum*, *Origanum munzurense*, *Origanum onites*, *Origanum pampaninii*, *Origanum petraeum*, *Origanum punonense*, *Origanum ramonense*, *Origanum rotundifolium*, *Origanum saccatum*, *Origanum scabrum*, *Origanum sipyleum*, *Origanum solymicum*, *Origanum symes*, *Origanum syriacum*, *Origanum vetteri*, *Origanum vogelii*, and *Origanum vulgare*.

In one embodiment, the at least one species of *Origanum* is *Origanum syriacum* and *Origanum ehrenbergii*.

In one embodiment, the at least one species of *Calendula* is selected from the group consisting of *Calendula eckerleinii*, *Calendula incana*, *Calendula lanzae*, *Calendula maritima*, *Calendula maroccana*, *Calendula meuselii*, *Calendula officinalis*, *Calendula palaestina*, *Calendula stellate*, *Calendula suffruticosa*, and *Calendula tripterocarpa*.

In one embodiment, the at least one species of *Calendula* is *Calendula officinalis*.

In one embodiment, the at least one species of *Matricaria* is selected from the group consisting of *Matricaria chamomilla*, *Matricaria courrantiana*, *Matricaria decipiens*, *Matricaria discoidea*, *Matricaria elongate*, *Matricaria grossheimii*, *Matricaria karjaginii*, *Matricaria lasiocarpa*, *Matricaria matricarioides*, *Matricaria occidentalis*, *Martricaria rupestris*, *Matricaria sevanesis*, *Matricaria subpolaris*, *Matricaria szowitzii*, *Matricaria tetragonosperma*, and *Matricaria transcaucasica*.

In one embodiment, the at least one species of *Matricaria* is *Matricaria chamomilla*.

In one embodiment, the at least one species of *Malva* is selected from the group consisting of *Malva mohileviensis*, *Malva moschata*, *Malva neglecta*, *Malva nicaeensis*, *Malva pacifica*, *Malva parviflora*, *Malva preissiana*, *Malva pseudolavatera*, *Malva pusilla*, *Malva qaiseri*, *Malva rotundifolia*, *Malva stipulacea*, *Malva subovata*, *Malva sylvestris*, *Malva transcaucasica*, *Malva tournefortiana*, *Malva trifida*, and *Malva verticillata*.

In one embodiment, the at least one species of *Malva* is *Malva sylvestris*.

In one embodiment, the at least one species of *Salvia* is selected from the group consisting of *Salvia absconditiflora*, *Salvia acuminata*, *Salvia adenocaulon*, *Salvia adenophora*, *Salvia adenophylla*, *Salvia adiantifolia*, *Salvia adoxoides*, *Salvia aegyptiaca*, *Salvia aequidens*, *Salvia aequidistans*, *Salvia aerea*, *Salvia aethiopis*, *Salvia africana*, *Salvia africana-lutea*, *Salvia alamosana*, *Salvia alariformis*, *Salvia alata*, *Salvia alatipetiolata*, *Salvia alba*, *Salvia albicalyx*, *Salvia albicaulis*, *Salvia albiflora*, *Salvia albimaculata*, *Salvia albocaerulea*, *Salvia alborosea*, *Salvia alexeenkoi*, *Salvia algeriensis*, *Salvia aliciae*, and *Salvia libanotica*.

In one embodiment, the at least one species of *Salvia* is *Salvia libanotica*.

In one embodiment, the aqueous extract of at least one species of *Calendula* is sourced from a leaf In one embodiment, the aqueous extract of at least one species of *Matricaria* is sourced from a flower.

In one embodiment, the aqueous extract of at least one species of *Malva* is sourced from a leaf.

In one embodiment, the aqueous extract of at least one species of *Salvia* is sourced from a leaf.

In one embodiment, the composition comprises: (i) 1-7 g/L of the essential oil extracted from at least one species of Origanum, (ii) 200-300 g/L of the aqueous extract of at least one species of *Calendula*; (iii) 200-300 g/L of the aqueous extract of at least one species of *Matricaria*, (iv) 200-300 g/L of the aqueous extract of at least one species of *Malva*; (v) 200-300 g/L of the aqueous extract of at least one species of *Salvia*; and (vi) 15-30 g/L of polyoxyethylene sorbitan, each based on the total volume of the composition.

A second aspect of the disclosure relates to a method for at least one of treating a vaginal infection, treating a vaginal inflammation, and reestablishing vaginal *lactobacilli* in a subject in need thereof, the method comprising administering an effective amount of the composition of the first aspect at least once daily to the subject in need thereof, where a source of the vaginal infection and/or the vaginal inflammation is at least one selected from the group consisting of *Trichomonas vaginalis, Gardnerella vaginalis,* and *Candida albicans*.

In one embodiment, the effective amount is in a range of 1-10 ml/kg body weight.

In one embodiment, the method reestablishes the vaginal *lactobacilli* and the subject is administered with the effective amount of the composition for one to 30 consecutive days, and the method further comprises measuring the vaginal *lactobacilli* count before the administering and/or measuring the vaginal *lactobacilli* count at least one week after the end of the administering.

A third aspect of the disclosure relates to a personal care product comprising the composition of the first aspect.

DETAILED DESCRIPTION OF THE
PREFERRED EMBODIMENTS

The present disclosure will be better understood with reference to the following definitions.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

The first aspect of the disclosure relates to a composition, comprising, consisting essentially of, or consisting of:
(i) 0.01-10 g/L, 0.1-8 g/L, 1-7 g/L, 2-6 g/L, or 3.5-5.5 g/L of an essential oil extracted from at least one species of Origanum;
(ii) 100-500 g/L, 150-400 g/L, or 200-300 g/L of an aqueous extract of at least one species of *Calendula*;
(iii) 100-500 g/L, 150-400 g/L, or 200-300 g/L of an aqueous extract of at least one species of *Matricaria*;
(iv) 100-500 g/L, 150-400 g/L, or 200-300 g/L of an aqueous extract of at least one species of *Malva*;
(v) 100-500 g/L, 150-400 g/L, or 200-300 g/L of an aqueous extract of at least one species of Salvia; and
(vi) 1-100 g/L, 5-80 g/L, 10-60 g/L, or 15-30 g/L of polyoxyethylene sorbitan, each based on a total volume of the composition. A pH of the composition may be a range of 4-5.5, 4.7-5.2, 4.5-4.9, or 4.6-4.8. The composition may be substantially free of a $C_1$-$C_6$ aliphatic alcohol, an aromatic alcohol, and a $C_3$-$C_{25}$ diol so that the composition can provide persistent antimicrobial protection without sensitizing and/or irritating the skin and or mucous membrane.

The composition consisting essentially of the above components can contain at least one additional component which does not substantially change the naturally occurring or a healthy population of microbiota. For example, the composition may contain emulsifiers, emollients, gel polymers, and/or a gelling agent, and the composition may still be useful for treating, vaginal infection/inflammation and/or reestablishing the vaginal *lactobacilli* count after the administering of the composition. Examples of these components are described hereinafter.

Essential oils are aromatic oily liquids obtained from plant materials (e.g., the whole plant, flowers, buds, seeds, leaves, twigs, stem, bark, fruits, roots, and combinations thereof). Essential oils are a rich source of biologically active compounds (e.g., hydrocarbons, such as monoterpenes and sesquiterpenes; and oxygenated compounds, such as monoterpenoids, sesquiterpenoids, esters, ethers, aldehydes, ketones, and oxides). Monoterpenes contain 10 carbons and are formed biosynthetically from two 5-carbon isoprene units. Exemplary monoterpenes include, without limitation, ocimene, myrcene, limonene, and geraniol. Sesquiterpenes contain 15 carbons and are formed biosynthetically from three 5-carbon isoprene units. Exemplary sesquiterpenes include, without limitation, chamazulene, farnesene, and caryophyllen. Monoterpenoids and sesquiterpenoids can be thought of as modified monoterpenes and sesquiterpenes, respectively, in which at least one methyl group has been moved or removed, at least one oxygen atom has been added, and/or at least one hydroxyl group has been added. Monoterpenoids and sesquiterpenoids may be the active compounds in the essential oils. Exemplary monoterpenoids, include, but are not limited to, menthol, thymol, and carvacrol. Exemplary sesquiterpenes include, without limitation, farnesol, nerolidol, bisabolol, apritone, santalol, zingiberol, and carotol. Derivatives of monoterpenoids and sesquiterpenoids, such as esters, with an increase in the total number of carbon atoms may also be included composition.

In the present disclosure, the composition comprises essential oil extracted from at least one species of *Origanum*. The at least one species of *Origanum* may be *Origanum acutidens, Origanum×adanense, Origanum×adonidis, Origanum akhdarense, Origanum amanum, Origanum×barbarae, Origanum bargyli, Origanum bilgeri, Origanum boissieri, Origanum calcaratum, Origanum compactum, Origanum cordifolium, Origanum cyrenaicum, Origanum dayi, Origanum dictamnus, Origanum×dolichosiphon, Origanum ehrenbergii, Origanum elongatum, Origanum floribundum, Origanum×haradjanii, Origanum haussknechtii, Origanum husnucan-baseri, Origanum hypericifolium, Origanum×intercedens, Origanum×intermedium, Origanum isthmicum, Origanum jordanicum, Origanum laevigatum, Origanum×leptocladum, Origanum libanoticum, Origanum majorana, Origanum×lirium, Origanum×majoricum, Origanum microphylhum, Origanum×minoanum, Origanum minutiflorum, Origanum munzurense, Origanum×nebrodense, Origanum onites, Origanum×pabotii, Origanum pampaninii, Origanum petraeum, Origanum punonense, Origanum ramonense, Origanum rotundifolium, Origanum saccatum, Origanum scabrum, Origanum sipyleum, Origanum solymicum, Origanum* symes, *Origanum syriacum, Origanum vetteri, Origanum vogelii, Origanum vulgare,* or combinations thereof. A hybrid name contains "×" which links the parents of the hybrid. Preferably, the at least one species of *Origanum* is *Origanum syriacum* and *Origanum ehrenbergii*. The weight ratio of the essential oil from *Origanum syriacum* to the essential oil from *Origanum ehrenbergii* may be in a range of 20:1 to 1:20, 10:1 to 1:10, 1:5 to 5:1, or 1:2 to 2:1. The essential oil of the at least one species of *Origanum* comprises at least 1%, at least 5%, at least 10%, at least 20%, at least 30%, at least 40%, at least 50%, at least 60%, at least 70%, at least 80%, at least 90%, or at least 95% carvacrol, based on a total weight of the essential oil. The composition may comprise 0.01-2 g/L, 0.02-1.8 g/L, 0.04-1.5 g/L, 0.06-1.2 g/L, 0.08-1 g/L, or 0.1-0.5 g/L of carvacrol, based on a volume of the composition.

Plant extracts, as defined herein, are not "essential oils" as noted above. The plant extract may be obtained from any of the plant parts including the leaves, pulp, seeds, stems, fruit and fruit seeds, as well as the whole plant. The plant extract comprises phytochemicals and/or metabolites that include, without limitation, alkaloids, flavonoids, saponins, carbohydrates, polysaccharides, terpenoids (e.g., monoterpenoids and sesquiterpenoids), steroids, sterols, phenols, tannins, anthraquinones, anthocyanins, amino acids, proteins, and vitamins.

The at least one species of *Calendula* may be *Calendula arvensis, Calendula denticulate, Calendula eckerleinii, Calendula incana, Calendula lanzae, Calendula maritima, Calendula maroccana, Calendula meuselii, Calendula officinalis, Calendula palaestina, Calendula stellate, Calendula suffruticosa, Calendula tripterocarpa,* or combinations thereof. Preferably, the at least one species of *Calendula* is *Calendula officinalis*. The aqueous extract of *Calendula* may be sourced from a leaf, a flower, a stem, a root, or combinations thereof. Preferably, the aqueous extract of *Calendula* is sourced from a leaf.

The aqueous extract of the at least one species of *Calendula* comprises at least 0.01%, at least 0.05%, at least 0.1%, at least 0.5%, at least 1%, at least 2%, or at least 5% of flavonoids, based on a total weight of the aqueous extract. The leaf of at least one species of *Calendula* may contain flavonoids in a range of 20-75 mg quercetin equivalent (QE)/g dried weight of the leaf 30-60 mg QE/g, or 40-50 mg QE/g (Rigane, G., Ben Younes, S., Ghazghazi, H., Ben Salem, R., Investigation into the biological activities and chemical composition of *Calendula officinalis* L. growing in Tunisia, International Food Research Journal, 20(6), 3001-3007 (2013), incorporated herein by reference in its entirety). The flower of at least one species of *Calendula* may contain 75-200 mg quercetin equivalent (QE)/g dried weight of the flower, 75-100 mg QE/g, or 75-200 mg QE/g. The flavonoids content in the aqueous extract may be determined spectrophotometrically using a method based on the formation of a complex formed between a flavonoid and aluminum. The complex has a maximum absorption at 510 nm according to Rigane et al. (Rigane, G., Ben. Salem, R., Sayadi, S. and Bouaziz, M. 2011. Phenolic composition, isolation and structure of a new deoxyloganic acid derivative from Dhokar and Gemri-Dhokar olive cultivars, Journal of Food Science 76: 965-973, incorporated herein by reference in its entirety). The composition may contain flavonoids extracted from the at least one species of Calendula in an amount of 0.01-1 g/L, 0.05-0.9 g/L, 0.1-0.8 g/L, or 0.3-0.6g/L, based on a volume of the composition.

The flavonoid may have a flavone skeleton, an isoflavan skeleton (for isoflavonoids), or a 4-phenylcoumarine skeleton (for neoflavonoids). Subgroups of flavonoids include, without limitation, anthoxanthin (e.g., flavone and flavonol), flavanone (hesperetin, naringenin, eriodictyol, homoeriodictyol), flavanonol (taxifolin, dihydrokaempferol), flavan (flavan-3-ol, flavan-4-ol, leucoanthocyanidin), anthocyanidins (cyanidin, delphinidin, malvidin, pelargonidin, peonidin, petunidin), isoflavones (genistein, daidzein, glycitein), isoflavanes, isoflavandiols, isoflavones, coumestans, and pterocarpans. Flavone includes luteolin, apigenin, and tangeritin. Flavonol includes quercetin, kaempferol, myricetin, fisetin, galangin, isorhamnetin, pachypodol, rhamnazin, pyranoflavonol, and furanoflavonol. Flavan-3-ol includes catechin, gallocatechin, catechin 3-gallate, gallocatechin 3-gallate, epicatechin, epigallocatechin, epicatechin 3-gallate, epigallocatechin 3-gallate, theaflavin (e.g., theaflavin-3-gallate, theaflavin-3'-gallate, and theaflavin-3,3'-digallate), and thearubigin. Flavonoids also include proanthocyanidins which are dimers, trimers, oligomers, or polymers of the flavanols.

The at least one species of *Matricaria* may be *Matricaria aserbaidshanica, Matricaria aurea, Matricaria australis, Matricaria brachyglossa, Matricaria breviradiata, Matricaria chamomilla, Matricaria courrantiana, Matricaria decipiens, Matricaria discoidea, Matricaria elongate, Matricaria grossheimii, Matricaria karjaginii, Matricaria lasiocarpa, Matricaria matricarioides, Matricaria occidentalis, Matricaria rupestris, Matricaria sevanensis, Matricaria subpolaris, Matricaria szowitzii, Matricaria tetragonosperma, Matricaria transcaucasica* or combinations thereof. Preferably, the at least one species of *Matricaria* is *Matricaria chamomilla*. The aqueous extract of at least one species of *Matricaria* may be sourced from a leaf, a flower, a stem, a root, or combinations thereof. Preferably, the aqueous extract of at least one species of *Matricaria* is sourced from a flower. The aqueous extract of at least one species of *Matricaria* comprises at least 0.01%, at least 0.05%, at least 0.1%, at least 0.5%, at least 1%, apt least 2%, or at least 5% of a sesquiterpene, based on a total weight of the aqueous extract. The sesquiterpene may be chamazulene, caryophyllene and valencene, α-farnesene (e.g., (E,E)-α-farnesene, (Z,E)-α-farnesene, (Z,Z)-α-farnesene, (E,Z)-α-farnesene) or β-farnesene ((E)-β-farnesene, (Z)-βfarnesene), zingiberene, humnlene, dictyophorine A, dictyophorine B, longifolene, and α-copaene. The leaf of at least one species of *Matricaria* may contain sesquiterpenes in a range of 100-1,000 µg/g, fresh weight of the leaf, 200-800 µg/g, or 500-700 mg µg/g (Irmisch, S., Krause, S. T., Kunert, G., Gershenzon, J., Degenhardt, J., and Köllner, T. G. The organ-specific expression of terpene synthase genes contributes to the terpene hydrocarbon. composition of chamomile essential oils, BMC Plant. Biology, 2012, 12:84, incorporated herein by reference in its entirety). The stem of *Matricaria* may contain sesquiterpenes in a range of 100-1,000 µg/g fresh weight of the stem, 200-800 µg/g, or 500-700 mg µg/g. The root of *Matricaria* may contain sesquiterpenes in a range of 100-1,000 µg/g fresh weight of the root, 150-700 µg/g or 200-500 mg µg/g. The composition may contain sesquiterpenes extracted from the at least one species of *Matricaria* in an amount of 0.01-1 g/L, 0.05-0.9 g/L, 0.1-0.8 g/L, or 0.5-0.78 g/L, based on a volume of the composition.

The at least one species of *Malva* may be *Malva aegyptia, Malva aethiopica, Malva alcea, Malva assurgentiflora, Malva brasiliensis, Malva canariensis, Malva cathayensis, Malva cretica, Malva dendromorpha, Malva hispanica, Malva microcarpa, Malva microphylla, Malva mohileviensis, Malva moschata, Malva neglecta, Malva nicaeensis,*

*Malva pacifica*, *Malva parviflora*, *Malva preissiana*, *Malva psendolavatera*, *Malva pusilla*, *Malva qaiseri*, *Malva rotundifolia*, *Malva stipulacea*, *Malva subovata*, *Malva sylvestris*, *Malva transcaucasica*, *Malva tournefortiana*, *Malva trifida*, *Malva verticillata*, or combinations thereof. Preferably, the at least one species of *Malva* is *Malva sylvestris*. The aqueous extract of at least one species of *Malva* may be sourced from a leaf, a flower, a stem, a root or combinations thereof. The aqueous extract of at least one species of *Malva* comprises at least 0.01%, at least 0.05%, at least 0.1%, at least 0.5%, at least 1%, at least 2%, or at least 5% phenols, based on a total weight of the aqueous extract. The amount of phenols may be measured by the Folin-Ciocalteau assay. Exemplary phenols include, without limitation rosmarinic acid, luteolin-7-O-β-glucopyranoside, gallic acid, 3,4-dihydroxybenzoic acid. 3,4-dihydroxyphenylacetic acid, chlorogenic acid, resorcinol, caffeic acid, 4-hydroxybenzoic acid, 3,5-dimethoxy-4-hydroxybenzoic acid, syringic acid, vanillic acid, 2,5-dihydroxybenzoic acid, p-coumaric acid, trans-4-hydroxy-3-methoxycinnamic acid, ferulic acid, rosmarinic acid, o-coumaric acid, trans-hydroxycinnamic acid, protocatechuic acid, naphtoresorcinol, salicylic acid, trans-cinnamic acid, carnosic acid, and carnosol. The leaf of *Malva* may contain phenols in a range of 20-30 mg gallic acid equivalent (GAE)/g dried weight of the leaf, 22-28 mg GAE/g, or 24-26 mg GAE/g (Beghdad, M. C., Benammar, C., Bensalah, F., Sabri, F., Belarbi, M., Chemat, F., Antioxidant activity, phenolic and flavonoid content in leaves, flowers, stems and seeds of mallow (*Malva sylvestris* L.) from North Western of Algeria, African Journal of Biotechnology. Vol. 13(3), pp. 486-491, Jan. 5, 2014, incorporated herein by reference in its entirety). The stem of *Malva* may contain phenols in a range of 1-10 mg gallic acid equivalent (GAE)/g dried weight of the stem, 2-8 mg GAE/g, or 2-6 mg GAE/g. The flower of *Malva* may contain phenols in a range of 1-10 mg gallic acid equivalent (GAE)/g dried weight of the flower, 4-8 mg GAE/g, or 6-7 mg GAE/g. The seed of *Malva* may contain phenols in a range of 1-10 mg gallic acid equivalent GAE/g dried weight of the seed, 2-8 mg GAE/g, or 3-6 mg GAE/g. Preferably, the aqueous extract of *Malva* is sourced from a leaf because it contains the highest amount of phenols compared to the stem, the flower, and the seed. The composition may contain phenols extracted from the at least one species of *Malva* in an amount of 0.01-1 g/L, 0.05-0.9 g/L, 0.1-0.8 g/L, or 0.2-0.5 g/L, based on a volume of the composition.

The at least one species of *Salvia* may be *Salvia absconditiflora*, *Salvia acuminata*, *Salvia adenocaulon*, *Salvia adenophora*, *Salvia adenophylla*, *Salvia adiantifolia*, *Salvia adoxoides*, *Salvia aegyptiaca*, *Salvia aequidens*, *Salvia aequidistans*, *Salvia aerea*, *Salvia aethiopis*, *Salvia africana*, *Salvia africana-lutea*, *Salvia alamosana*, *Salvia alariformis*, *Salvia alata*, *Salvia alatipetiolata*, *Salvia alba*, *Salvia albicalyx*, *Salvia albicaulis*, *Salvia albiflora*, *Salvia albimaculata*, *Salvia albocaerulea*, *Salvia alborosea*, *Salvia alexeenkoi*, *Salvia algeriensis*, *Salvia aliciae*, *Salvia alvajaca*, *Salvia amethystina*, *Salvia amissa*, *Salvia amplexicaulis*, *Salvia amplicalyx*, *Salvia amplifrons*, *Salvia anastomosans*, *Salvia anatolica*, *Salvia andreji*, *Salvia anguicoma*, *Salvia angulata*, *Salvia angustiarum*, *Salvia apiana*, *Salvia apparicii*, *Salvia appendiculata*, *Salvia arabica*, *Salvia aramiensis*, *Salvia aborescens*, *Salvia arbuscula*, *Salvia arduinervis*, *Salvia arenaria*, *Salvia areolata*, *Salvia argentea*, *Salvia ariana*, *Salvia aridicola*, *Salvia aristata*, *Salvia arizonica*, *Salvia arthrocoma*, *Salvia articulata*, *Salvia aspera*, *Salvia asperata*, *Salvia asperiflora*, *Salvia assurgens*, *Salvia atrocalyx*, *Salvia atrocyanea*, *Salvia atropaenulata*, *Salvia atropatana*, *Salvia atropurpurea*, *Salvia atrorubra*, *Salvia aucheri*, *Salvia aurita*, *Salvia austriaca*, *Salvia austromelissodora*, *Salvia axillaris*, *Salvia axilliflora*, *Salvia ayavacensis*, *Salvia ayayacensis*, *Salvia aytachii*, *Salvia azurea*, *Salvia bahorucona*, *Salvia baimaensis*, *Salvia balansae*, *Salvia balaustina*, *Salvia baldshuanica*, *Salvia ballotiflora*, *Salvia ballsiana*, *Salvia bariensis*, *Salvia barrelieri*, *Salvia bazmanica*, *Salvia beckeri*, *Salvia benthamiana*, *Salvia betulifolia*, *Salvia bifidocalyx*, *Salvia biserrata*, *Salvia blancoana*, *Salvia blepharophylla*, *Salvia boegei*, *Salvia bogotensis*, *Salvia booleana*, *Salvia borjensis*, *Salvia bowleyana*, *Salvia brachyantha*, *Salvia brachyloba*, *Salvia brachyloma*, *Salvia brachyodon*, *Salvia brachyodonta*, *Salvia brachyphylla*, *Salvia bracteata*, *Salvia brandegeei*, *Salvia breviconnectivata*, *Salvia breviflora*, *Salvia brevilabra*, *Salvia brevipes*, *Salvia broussonetii*, *Salvia buchananii*, *Salvia bucharica*, *Salvia buchii*, *Salvia bulleyana*, *Salvia bullulata*, *Salvia caaguazuensis*, *Salvia cabonii*, *Salvia cabulica*, *Salvia cacaliifolia*, *Salvia cadmica*, *Salvia caespitosa*, *Salvia calaminthifolia*, *Salvia calcicola*, *Salvia californica*, *Salvia calolophos*, *Salvia camarifolia*, *Salvia campanulata*, *Salvia campicola*, *Salvia camporum*, *Salvia campyladonta*, *Salvia canariensis*, *Salvia candelabrum*, *Salvia candicans*, *Salvia candidissima*, *Salvia canescens*, *Salvia capillosa*, *Salvia carbonoi*, *Salvia cardenasii*, *Salvia cardiophylla*, *Salvia carduacea*, *Salvia carnea*, *Salvia cassia*, *Salvia castanea*, *Salvia cataractarum*, *Salvia caudate*, *Salvia cavaleriei*, *Salvia caymanensis*, *Salvia cedronella*, *Salvia cedrosensis*, *Salvia ceratophylla*, *Salvia cerradicola*, *Salvia chalarothyrsa*, *Salvia chamaedryoides*, *Salvia chamelaeagnea*, *Salvia chanryoenica*, *Salvia chapadensis*, *Salvia chapalensis*, *Salvia chiapensis*, *Salvia chicamochae*, *Salvia chienii*, *Salvia chinensis*, *Salvia chionantha*, *Salvia chionopeplica*, *Salvia chionophylla*, *Salvia chloroleuca*, *Salvia chorassanica*, *Salvia chrysophylla*, *Salvia chudaei*, *Salvia chunganensis*, *Salvia cilicica Boiss*, *Salvia cinica Migo*, *Salvia cinnabarina*, *Salvia circinnata*, *Salvia clarendonensis*, *Salvia clausa*, *Salvia clevelandii*, *Salvia clinopodioides*, *Salvia coahuilensis*, *Salvia coccinea*, *Salvia cocuyana*, *Salvia codazziana*, *Salvia coerulea*, *Salvia cognate*, *Salvia colonica*, *Salvia columbariae*, *Salvia comayaguana*, *Salvia compar*, *Salvia compressa*, *Salvia compsostachys*, *Salvia concolor*, *Salvia confertiflora*, *Salvia congestiflora*, *Salvia connivens*, *Salvia consimilis*, *Salvia consobrina*, *Salvia corazonica*, *Salvia cordata*, *Salvia coriana*, *Salvia corrugate*, *Salvia costaricensis*, *Salvia costata*, *Salvia coulteri*, *Salvia crinigera*, *Salvia crucis*, *Salvia cruikshanksii*, *Salvia cryptoclada*, *Salvia cryptodonta*, *Salvia cuatrecasana*, *Salvia cubensis*, *Salvia curta*, *Salvia curticalyx*, *Salvia curtiflora*, *Salvia curviflora*, *Salvia cuspidate*, *Salvia cyanantha*, *Salvia cyanescens*, *Salvia cyanicalyx*, *Salvia cyanocephala*, *Salvia cyanotropha*, *Salvia cyclostegia*, *Salvia cylindriflora*, *Salvia cynica*, *Salvia libanotica*, or combinations thereof. Preferably, the at least one species of *Salvia* is *Salvia libanotica*. The aqueous extract of at least one species of *Salvia* may be sourced from a leaf, a flower, a stem, a root, or combinations thereof. Preferably, the aqueous extract of at least one species of *Salvia* is sourced from a leaf. The leaf of at least one species of *Salvia* may contain the aforementioned phenols in a range of 40-250 mg gallic acid equivalent (GAE)/g dried weight of the leaf, 50-230 mg GAE/g, or 80-160 mg GAE/g (Bakkour, Y., Douhaibi, A. E., El-Achi, A., Al-Houmayssi. F., Al-Houmayssi, O., El-Nakat, H., El-Omar, F., Chemical composition and Antioxidant activities of the ethanolic extract of Salvia libanotica growing in Lebanon, International Journal of Phytopharmacy, Vol. 3 (4), pp. 76-80, July-August 2013, incorporated herein by reference in its entirety.) The stem of at least one species of *Salvia* may contain phenols in a range of 40-180 mg gallic acid equivalent (GAE)/g dried weight of the stem, 80-150 mg GAE/g, or 110-130 mg GAF/g. The flower of at least one species of *Salvia* may contain phenols in a range of 20-160 mg gallic acid equivalent (GAE)/g dried weight of the flower, 50-150 mg GAE/g, or 100-145 mg GAE/g. The seed of at least one species of *Salvia* may contain phenols in a range of 1-10 mg gallic acid equivalent (GAE)/g dried weight of the seed, 2-8 mg GAE/g, or 3-6 mg GAE/g. Preferably, the aqueous extract of at least one species of *Salvia* is sourced from a leaf because it contains the highest amount of phenols compared to the stem, the flower, and the seed. The composition may contain phenols extracted from the at least one species of *Salvia* in an amount of 0.01-1 g/L, 0.05-0.9 g/L, 0.1-0.8 g/L, or 0.4-0.6 g/L, based on a volume of the composition.

The composition may comprise 1-100 g/L, 5-80 g/L, 10-60 g/L, or 15-30 g/L of an emulsifier, based on the total volume of the composition. The emulsifier stabilizes the mixture of the essential oil and aqueous extracts. Exemplary emulsifier includes, without limitation, emulsifying waxes (e.g. Incroquat® (fatty quaternary ammonium salt and cetyl alcohol-based wax) and Polawax® (cetearyl alcohol and polysorbate-based wax)), and polyoxyethylene sorbitan.

The composition may further comprise 4-100 g/L, 10-90 g/L, 20-80 g/L, or 50-70 g/L of an emollient, based on the total volume of the composition. The emollient absorbs and retains the water vapor in the air thereby drawing the water vapor into or beneath the point of application. Exemplary emollients include, without limitation urea, aloe vera gel, an α-hydroxy acid (e.g., lactic acid), glyceryl triacetate, a polymeric polyol (e.g., polydextrose), a sugar alcohol (e.g., glycerol/glycerin, sorbitol, xylitol, and maltitol), a PEG-20 almond glyceride, an ethoxylated or propoxylated methyl glucose ether (e.g., Glucam® P-20, Glucam® E-10, Glucam® P-10, Glucam® E-20, Glucam® P-20 distearate), cetyl acetate, acetylated lanolin alcohol (e.g., acetulan®), cetyl ether (e.g.. PPG-10), myristyril ether (e.g., PPG-3), hydroxylated milk glycerides (e.g., Cremerol® HMG), polyquaternium compounds (e.g., U-care® compounds), copolymers of dimethyl dialyl ammonium chloride and acrylic acid (e.g., Merquat®), dipropylene glycol methyl ethers (e.g., Dowanol® DPM, Dow Coming), and polypropylene glycol ethers (e.g., Ucon® 50-HB-600, Union Carbide). Other suitable emollients may include hydrocarbon-based emollients, such as petrolatum or mineral oil; fatty ester-based emollients, such as methyl, isopropyl and butyl esters of fatty acids (e.g., isopropyl palmitate, isopropyl myristate, isopropyl isostearate, diisopropyl sebacate); and $C_{12}$-$C_{16}$ fatty alcohol lactates, such as cetyl lactate and lauryl lactate. Additional fatty ester-based emollients include, isostearyl isostearate, propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, and isohexyl laurate. Additional useful emollients include lanolin, olive oil, cocoa butter, and shea butter. Preferably, the emollient is glycerin.

The composition may further comprise 0.5-100 g/L, 1-80 g/L, 5-50 g/L, or 10-30 g/L of a pH adjuster to adjust the pH of the composition to the desired aforementioned range. For example, when the pH of the composition is more acidic than pH 4.0, a basic pH adjuster may be added to increase the pH. Exemplary basic pH adjusters include, without limitation, ammonia, mono-, di- and tri- alkyl amines (e.g., trimethylamine and isopropylamine); mono- , di- and tri- alkanolamines (e.g., monoethanolamine, diethanolamine, and triethanolamine); alkali metal and alkaline earth metal hydroxides (e.g., ammonia, sodium hydroxide, potassium hydroxide, and lithium hydroxide); alkali metal and alkaline earth metal bicarbonates (e.g., ammonium bicarbonate, sodium bicarbonate, potassium bicarbonate, and lithium bicarbonate). Preferably, the basic pH adjuster is sodium bicarbonate. In some embodiments, where the pH of the composition is more alkaline than 5.5, an acid pH adjuster is added to lower the pH. Exemplary acid pH adjusters include, without limitation, such as mineral acids and polycarboxylic acids (e.g., hydrochloric acid, nitric acid, phosphoric acid, sulfuric acid, citric acid, glycolic acid, and lactic acid); vitamins (e.g., vitamin A, vitamin E and vitamin C); polyamino acids and salts (e.g., ethylenediamine tetraacidic acid (EDTA)). Preferably, the acid pH adjuster is citric acid.

In some embodiments, the composition further comprises an antibacterial compound. As used herein, the term "antibacterial compound" refers to a compound that inhibits or prevents the growth of bacterial cells. The antibacterial compound may be present at an amount of 0.1-20 g/L, 0.5-15 g/L, 1-10 g/L, or 2-5 g/L, based on a total volume of the composition. Exemplary antibacterial compounds include, without limitation, ampicillin, flucloxacillin, amoxicillin, gentamicin, amikacin, kanamycin, neomycin, netilmicin, tobramycin, paromomycin, streptomycin, spectinomycin, tetracycline, penicillin, erythromycin, clindamycin, mupirocin, bacitracin, polymyxin B, and doxycycline. The composition may be useful for treating a bacterial infection. A source of the bacterial infection is at least one of *Gardnerella vaginalis, Mycobacterium tuberculosis, Clostridium difficile, Listeria monocytogenes, Neisseria meningitides, Vibrio cholera, Enterococcus faecalis, Clostridium botulinum, Clostridium tetani, Bacillus cereus, Salmonella enterica, Bacillus anthracis, Bacillus subtilis, Staphylococcus aureus, Escherichia coli, Proteus species,* and *Pseudomonas aeruginosa.*

In some embodiments, the composition further comprises an antifungal compound, which may be amphotericin B, itraconazole, posaconazole, voriconazole, fluconazole, flucytosine, terbinafine, posaconazole, isavuconazole, griseofulvin, ketoconazole, miconazole, nystatin, thiomersal, itriconazole, or clotrimazole. The antifungal compound may be present at an amount of 0.1-20 g/L, 0.5-15 g/L, 1-10 g/L, or 2-5 g/L, based on a total weight of the composition. The composition may be useful for treating a fungal infection. A source of the fungal infection is yeast and/or at least one fungus such as *Candida albicans, Cryptococcus neoformans, Cryptococcus gattii, Aspergillus fumigatus, Aspergillus flavus, Histoplasma capsulatum, Coccidioides immitis, Coccidioides posadasii, Blastomyces dermatitidis, Sporothrix schenckii, Pneumocystis jirovecii, Histoplasma capsulatum, Magnaporthe oryzae, Botrytis cinerea,* species within the *Puccinia* genus, *Fusarium graminearum, Fusarium oxysporum, Fusarium equiseti, Blumeria graminis, Mycosphaerella graminicola,* species within the *Colletotrichum* genus, *Ustilago maydis, Melampsora lini, Phakopsora pachyrhizi, Rhizoctonia solani, Cochliobolus lunatus, Rhizopus oryzae,* or *Phoma sorghina.*

In some embodiment, the composition further comprises an antimicrobial compound. As used herein, the term "antimicrobial compound" refers to a compound that inhibits or prevents the proliferation of pathogens which are microorganisms that cause diseases. Exemplary pathogens include, without limitation, yeast, bacteria, fungi, viruses, algae, protozoa, and parasites. The antimicrobial compound may be a synthetic antimicrobial agent which may be a quaternary ammonium compound (e.g.., benzalkonium chloride, dequalinium chloride, and benzethonium chloride), iodopropynylbutyl carbamate, iodophors (e.g. povidone-iodine), iodine, benzoic acid, dihydroacetic acid, propionic acid, sorbic acid, methyl paraben, ethyl paraben, propyl paraben, butyl paraben, cetrimide, glutaraldehyde, phenols (including chlorinated phenols such as triclosan, chloroxylenol, and chlorocresol), octenidine dihydrochloride, bronopol, foscamet, Vantocil® (polyiminoimidocarbonyliminoimidocarbonyl-iminohexamethylene) hydro-chloride, polyhydroxymethylbiguanide (PHMB) and biguanides (polyhexamethylene biguanide, chlorhexidine and chlorhexidine salts such as chlorhexidine palmitate, chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-alpha-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, and chlorhexidine embonate).

The composition may include one or more solvents, including but not limited to water and vegetable oil (e.g., olive oil, almond oil, avocado oil, basil oil, primrose oil, peanut oil, safflower oil, sesame oil, soya or soy bean oil, wheat germ oil).

The composition of topical application can be produced in liquid or semi-solid formulation. The composition may be in a form of an emulsion, a cream; a solution, a gel (e.g., a cream gel or a hydrogel), or a suspension/dispersion. In other embodiments, the composition may be in a form of a multiple emulsion, such as coil and/or silicone in water emulsions, water-in-oil and/or silicone emulsions, water/oil/ water or water/silicone/water type emulsions, and oil/water/ oil or silicon/water/silicon type emulsions. The composition maybe a leave-on type or a rinse-off-type. Preferably, the composition is a rinse-off type.

Essential oils are volatile and therefore it is desirable that the composition is incorporated in a suitable formulation in which it is stable at higher temperature and over a long period of time. Accordingly, the composition may optionally comprise a hydrophilic or hydrophobic gel forming polymer. Suitable hydrophilic gel polymers include, but are not limited to, hydroxypropylmethyl cellulose, cationic hydroxyethyl cellulose (U-care® polymers), ethyl cellulose, hydroxypropyl cellulose, hydroxymethyl cellulose, carboxy methyl cellulose, polyethylene oxide (polyox® resins), chitosan pyrrolidone carboxylate (Kytamer® PC), silica gel, and carbomerpolymers. Suitable hydrophobic gel polymers include, but are not limited to, silicone polymers, for example polydimethylsiloxane polymer (Dow Corning® 225 silicone fluid), dimethiconol fluid in dimethicone (Dow Corning® 1403 silicone fluid), cyclomethicone and dimethicone copolyl (Dow Coming® 3225C and Q2-5220 silicone fluids), silicone glycol (BASF® 1066 DCG polyol), and KSG® series silicone gels (Shin-etsu).

In some embodiments, the composition is in a form of a gel. The composition may further comprise 0.01-10 g/L, 0.05-8 g/L, 0.1-5 g/L, or 0.3-2 g/L of a gelling agent. The gelling agent may be a natural gelling agent. Exemplary natural gelling agents include, without limitation, natural gums (e.g. guar gum, xanthum gum, locust bean gum, also known as E410, a natural gum from the seeds of the Carob tree), polysaccharides (e.g., alginic acid (E400), sodium alginate (E401), potassium alginate (E402), ammonium alginate (E403), calcium alginate (E404, a polysaccharide from brown algae), agar (E406, a polysaccharide obtained from red seaweeds), carrageenan (E407, a polysaccharide obtained from red seaweeds), pectin (E440, a polysaccharide obtained from apple or citrus-fruit), and proteins (e.g., gelatin which is also known as E441 and made by partial hydrolysis of animal collagen).

The composition may be substantially free of a $C_3$-$C_5$ alkanediol, a $C_1$-$C_6$ aliphatic alcohol, and an aromatic alcohol to reduce skin sensitivity. As used herein, "substantially free" refers to the composition containing less than 0.1 g/L, less than 0.05 g/L, less than 0.01 g/L, less than 0.005 g/L, or less than 0.001 g/L of the $C_3$-$C_{25}$ alkanediol, the $C_1$-$C_6$ aliphatic alcohol, and the aromatic alcohol, based on a total volume of the composition. Exemplary $C_3$-$C_{25}$ alkanediols include, but are not limited to, diglycerol, diethylene glycol, triethylene glycol, dipropylene glycol, tripropylene glycol, hexylene glycol, butylene glycol, butanediol, pentanediol, hexanediol, heptanediol, octanediol, nonanediol (e.g., 1,9 nonanediol), decanediol 1,2-decanediol and 1,10-decanedial), idecanediol, dodecanediol 1,2-dodecanediol, 1,12-dodecanediol, cyclododecanediol), 1,13-tridecanediol, 1,2-tetradecanediol, 1,14-tetradecanediol, 1,15 -pentadecanediol, 1,16-hexadecanediol, 1,17-heptadecanediol, 1,18-octadecanediol, 1,19- nonadecanediol, 1,20-eicosanediol, 1,21-heneicosanediol, 1,22-docosanediol, 1,23-tricosanediol, 1,24-tetracosanediol, 1,25-pentacosanediol, and propanediol (e.g., 1,3 propanediol or Zemea®). Exemplary $C_1$-$C_6$ aliphatic alcohols include methanol, ethanol, n-propanol, isopropyl alcohol, 2-methyl-2 propanol, tert-butanol, pentanol, hexanol, or isomers thereof. Exemplary aromatic alcohols include, without limitation, phenoxyethanol, benzyl alcohol, 1-phenoxy-2-propanol, and/or phenethyl alcohol. As used herein, the term "aromatic alcohol" refers to an organic compound in which the hydroxyl group is bonded indirectly to an aromatic hydrocarbon group (i.e., the hydroxyl group may be separated from the aromatic hydrocarbon group by at least one carbon atom). On the contrary, in phenols, the hydroxyl group is bonded directly to an aromatic carbon atom.

A method of preparing the composition is described hereinafter. The plant for the essential oil and/or the aqueous extract may be at any growth stage, e.g. at a flowering stage when the flower and/or one or more non-flower parts (e.g. leaf, stem, and root) may be used to make the essential oil and/or the aqueous extract, or alternatively, at a non-flowering stage, when one or more non-flower parts may be used to make the essential oil and/or the aqueous extract.

The essential oil of the at least one species of *Origanum* may be obtained by expression, fermentation, distillation, steam distillation, pressing organic extraction, or additional extraction methods known to those familiar in the art.

The aqueous extracts may be prepared as follows. The plant part(s) of interest may be collected and then washed thoroughly, preferably twice/thrice with tap water, to remove both epiphytes and necrotic plants; preferably followed by washing with sterile distilled water to remove associated debris if any. The clean and fresh plant parts may be sun-dried or dried in the shade for 5-25 days, or preferably 7-20 days, or more preferably 10-15 days, and then finely cut, or preferably powdered/pulverized using, for example, a domestic blender. The dried finely cut or powdered plant parts may be mixed with water (e.g., deionized distilled water) in an amount of 0.01-5 g/ml, 0.05-3 g/ml, 0.1-2 g/ml or 0.2-1 g/ml of water. The resulting mixture may be heated at a temperature of 60-100° C., 70-90° C., or 75-85° C. for 1-30 minutes, preferably 5-25 minutes, or more preferably 10-20 minutes. In some embodiments, the hot water percolation method is used. The resulting infusion is then preferably filtered thoroughly until no insoluble material appears in the aqueous extract. In another embodiment, a solvent other than water, e.g. a mixture of ethyl acetate and methanol, may be used to make the plant extract.

A weight ratio of the essential oil to a total weight of the combined aqueous extracts may be in a range of 1:10 to 1:1,000, 1:30 to 1:1600, 1:50 to 1:500, or 1:90 to 1:300. A weight ratio of the aqueous extract from at least one species of *Calendula* to the aqueous extract of the at least one species of *Matricaria* may be in a range of 5:1 to 1:5, 4:1 to 1:4, 3:1 to 1:3, or 1:2 to 2:1. A weight ratio of the aqueous extract from at least one species of *Calendula* to the aqueous extract of the at least one species of Malva may be in a range of 5:1 to 1:5, 4:1 to 1:4, 3:1 to 1:3, or 1:2 to 2:1. A weight ratio of the aqueous extract, from at least one species of *Calendula* to the aqueous extract of the at least one species of *Salvia* may be in a range of 5:1 to 1:5, 4:1 to 1:4, 3:1 to 1:3, or 1:2 to 2:1. In some embodiments, the composition comprises equal amounts of each aqueous extract. In some embodiments, the total weight of the aqueous extracts makes up at least 60%, at least 70%, at least 80%, at least 90%, or at least 95% of the total weight of the composition.

The aqueous extracts may be mixed with the emollient, the pH adjuster, and/or other aforementioned additives to form a first mixture. The essential oil may be mixed with the emulsifier to form a second mixture which is then added to the first mixture with agitation. Exemplary forms of agitation include sonication (e.g., with a ultrasonic bath or an ultrasonic probe), stirring, and shaking (e.g., with a shaker). The composition may be stirred manually, magnetically, or mechanically with a mechanical stirrer.

The second aspect of the disclosure relates to a method for at least one of treating a vaginal infection, treating a vaginal inflammation, and reestablishing vaginal *lactobacilli* in a subject in need thereof. Exemplary vaginal infection includes, without limitation, yeast infection, bacterial vaginosis, trichomonas, chlamydia vaginitis, noninfectious vaginitis, vulvodynia, and virial vaginosis.

As used herein, the terns "treat", "treatment", and "treating" in the context of the administration of the composition to a subject in need thereof refer to the reduction or inhibition of the progression and/or duration of a disease, the reduction or amelioration of the severity of the disease, and/or the amelioration of one or more symptoms thereof resulting from the administration the composition. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease, and relieving the disease (causing regression of the disease). With regard to the disease, these terms simply mean that one or more of the symptoms of the disease will be reduced. Such terms may refer to one, two, three, or more results following the administration of the composition: (1) a stabilization, reduction (e.g. by more than 10%, 20%. 30%, 40%, 50%, preferably by more than 60% of the population of the pathogen population before administration), or elimination of the pathogens, (2) inhibiting the growth of pathogens, (3) relieving to some extent (or, preferably, eliminating) one or more symptoms associated with a pathology related to or caused in part by pathogen infection, (4) an increase in disease-free, relapse-free, progression-free duration, or rate, (5) a decrease in hospitalization rate, (6) a decrease in hospitalization length, and (7) a stabilization or reduction (e.g. by at least 10%, 20%, 30%, 40%, 50%, 60%, 70%, preferably at least 80% relative to the initial growth rate) in the growth of pathogen population.

The terms "patient", "subject", and "individual" are used interchangeably. As used herein, they refer to individuals suffering from a disease. None of the terms require that the individual be under the care and/or supervision of a medical professional. The subject may be a mammal, such as a human; a non-human primate, such as a chimpanzee, and other apes and monkey species; a farm animal, such as a cow, a horse, a sheep, a goat, and a pig; a domestic animal, such as a rabbit, a dog, and a cat; a laboratory animal including a rodent, such as a rat, a mouse, and a guinea pig; and the like. In preferred embodiments, the subject is a human. In some embodiments, the subject is a mouse. In one embodiment, healthy mice are infected with the pathogens for testing the efficacy of the composition. For example, each mouse may be infected by injecting 1,000-100,000 pathogen cells, 3,000-50,000 pathogen cells, or 7000-20,000 pathogen cells.

The method comprising administering an effective amount of the composition at least once daily, 1-4 times daily, or 2-4 times daily to the subject.

The terms "effective amount", "therapeutically effective amount", or "pharmaceutically effective amount" refer to that amount of the composition being administered which will relieve to some extent one or more of the symptoms of the disease being treated. The result can be reduction and/or alleviation of the signs, symptoms, or causes of a disease, or any other desired alteration of a biological system.

For example, the administration may be once, twice (e.g., every 12 hours), or thrice (e.g., every 7-8 hours) daily. The terms "administer", "administering", "administration", and the like, as used herein, refer to the methods that may be used to enable delivery of the composition to the desired site of biological action.

A source of the vaginal infection and/or the vaginal inflammation is at least one selected from the group consisting of herpes simplex virus, *Chlamydia trachomatis, Trichomonas vaginalis, Gardnerella vaginalis,* and *Candida albicans*. The effective amount is in a range of 1-10 ml/kg body weight, 2-7 ml/kg, or 3-5 ml/kg. For example, for a human subject with a body weight of 50 kg, the effective amount will be in a range of 50-500 ml, 100-350 ml, or 150-250.

In some embodiments, the method treats a vaginal infection and/or a vaginal inflammation. The vaginal infection and/or inflammation may be reduced to not more than 20%, not more than 10%, not more than 5%, or not more than 1% compared to untreated subjects. The reduction in infection and/or inflammation may be determined by performing a vagina smear (i.e., wet prep or vaginal wet mount) and observing the sample from the vaginal smear under a microscope. In some embodiments, the sample may be cultured in appropriate cell culture medium and then observed under a microscope, Exemplary cell culture medium include, without limitation, Mueller-Hinton agar, brain-heart infusion, Sabouraud dextrose broth, and Diamond TYM. The cell culture medium may be supplemented with serum from horses and/or humans, glucose, and dyes (e.g., methylene blue). The reduction may be evident 0.5-10 days, 1-8 days, or 1-5 days after the end of the administration.

In one embodiment, the method reestablishes the vaginal lactobacilli. The subject is administered with the effective amount of the composition for 1-30, 2-20, 2-7, 3-6, or 3-5 consecutive days. The mucous membrane and the composition may in contact for 1-20 minutes, 2-10 minutes, or 4-6 minutes. The vaginal lactobacilli count may be measured before the administration and after waiting for at least one week, 2-6 weeks, or 3-5 weeks from the end of the administering. The amount of vaginal lactobacilli before the administration (i.e., the initial amount) may be in a range of $0.5 \times 10^6$–$10 \times 10^6$/g of mucous membrane tissue obtained from the subject, $1 \times 10^6$ to $7 \times 10^6$/g, $2 \times 10^6$ to $5 \times 10^6$/g, or $3 \times 10^6$ to $4 \times 10^6$/g. The amount of vaginal lactobacilli measured at the end of the waiting period may be the same or substantially the same as the initial at count of vaginal lactobacilli. As used herein, the phrase "substantially the same" refers to at least 80%, at least 85%, at least 90%, at least 95% of the initial amount of vaginal lactobacilli.

In some embodiments, the efficacy of the composition is tested in vitro. The protozoa cells may be loaded into wells of a microtiter plate. A loading density may be 2,000-10,000 cells/ml, 3,000-7,000 cells/ml, or 4,000-6,000 cells/ml. The composition may be added to each well in an amount of 10-500 µL, 50-300 µL, or 100-200 µl. The composition may be incubated with the cells for 10-90 hours, 20-60 hours, or 30-50 hours at a temperature of 30-40° C., 32-39° C., or 35-38° C. and in the presence of oxygen. The composition may reduce the number of cells with motility to not more than 20%, not more than 15%, not more than 10%, or not more than 5% of an initial number of cells (i.e., before contacting the cells with the composition). As used herein, the term "motility" refers to the ability of the cells to move by themselves. The cells may move with the help of flagella, cilia, or pseudopodia. In one embodiment, the flagellar motility may be observed with a microscope such as an inverted-phase contrast microscope.

In some embodiments, the susceptibility testing of the microorganism may be carried out with a broth dilution method (e.g. microdilution or macrodilution), an agar dilution method, an agar well diffusion method, or a disc diffusion method. Preferably, the disc diffusion method is used. In one embodiment, not more than 20%, not more than 10%, not more than 5%, or not more than 1% of the microorganisms are resistant to the composition. As used herein, the term "resistant" means the growth of the microorganisms is not inhibited by the composition. In one embodiment, at least 60%, at least 70%, at least 80%, at least 90% of the microorganisms are susceptible to the composition. As used herein, the term "susceptible" refers to the growth of the microorganism is inhibited by the composition. An amount of the composition that inhibits the growth of the microorganism may be 1-100 µL, 10-70 µL, 15-40 µL, or 18-25 µL. An initial amount of the microorganism may be in a range of 100-10,000 cells/100 µL of culture medium, 300-5,000 cells/100 µL of culture medium, or 500-1,000 cells/100 µL of culture medium.

A third aspect of the disclosure relates to a personal care product comprising the composition. As used herein, the term "care" refers to the improvement and/or the maintenance of the qualities of the mucous membrane. These qualities are subject to improvement and/or are maintained through care of the mucous membranes both in healthy subjects as well as those which present diseases and/or disorders of the mucous membranes, such as and not restricted to, vaginitis. In some embodiments, the composition is a skin care product winch is useful for treating ulcers and lesions on the skin, psoriasis, dermatitis and acne or rosacea. Exemplary personal care products include vaginal douche, bar soap, liquid soap (e.g., hand soap), hand sanitizer (including rinse off and leave-on and aqueous-based hand disinfectants), preoperative skin disinfectant, cleansing wipes, disinfecting wipes, body wash, acne treatment products, antifungal diaper rash cream, antifungal skin cream, deodorant, antimicrobial creams, and topical cream. The composition may also be useful as a wound care item, such as, but not limited to, wound healing ointments, creams, and lotions.

EXAMPLE 1

Preparation of the Composition

The amount of the water extract of the four plants to the amount of the essential oil of Origanum syriacum to the amount of the essential oil of Origanum ehrenbergii to the amount of polyoxyethylene sorbitan (an emulsifier) was 98.0/0.2/0.2/1.6 (v/v).

The water extract of plants was composed of equal volumes of the four extracts. The ground leaves of the plants were subjected to decoction in hot water (1 g of plant part per 5 ml of water) at 80° C. for 15 minutes, except for Matricaria chamomilla (the flower was used. instead of the leaves). The medicinal benefits and the references, related to each water extract, are included in the brackets: Calendula officinalis (antimicrobial and anti-inflammatory), Matricaria chamomilla (antibacterial and anti-inflammatory), Malva sylvestris (emollient/moistening/anti-inflammatory), and Salvia libonitica (antioxidant, anticancer, and antimicrobial) (Basch et al., Journal of Herbal Pharmacotherapy, Vol 6, pp 135-159, 2006; Thorne Research, alternative Medicine Revieweu, Vol 13, pp 58-62, 2008; Prudente et al., Chemistry and Toxicology, Vol 58, pp 324-331, 2013; Srivastava et al, Molecular Medicine Reports, pp. 895-901, doi: 10.3892/nunr.2010.377, 2010; Gali-Muhtaseb et al., Journal of Ethnopharmacology, Vol 71, pp 513-520, 2000; Itani et al., Cancer Biology and Therapy, Vol 7, pp. 1765-1773, 2008; and Zhiming et al., Journal of Applied Pharmaceutical Science, Vol 3, pp 122-127, 2013, each incorporated herein by reference in their entirety). The main ingredients in the water extract of each of the four herbs are included in the brackets: Calendula officinalis (flavonoids), Matricaria chamomilla (sesquiterpenes), Malva sylvestric (phenols), and Salvia libonitica (phenols). The main ingredient in the essential oils of Origanum syriacum and Origanum ehrenbergii is carvacrol, an active ingredient against microbes (Baser, Current Pharmaceutical Design, Vol 14 (29), pp 3106-3119, 2008; and Lakis et al., Farmacia, Vol 60, pp 857-865, 2012), each incorporated herein by reference in their entirety). The food grade emulsifier, polyoxyethylene sorbitan, created an oil-in-water emulsion at a concentration of 0.05 to 9.0%, preferably 1.6%. The pH of the vaginal douche was adjusted by sodium bicarbonate buffer or citrate/citric acid buffer to reach a pH favorable to beneficial vaginal microbiota. The pH was 4.0-5.5, and preferably 4.75. Safe softeners, such as glycerin, can be added to the composition at a concentration of 0.4-10.0%, preferably 6.8%.

The following lists the amount of the major ingredients in the composition in a 100-liter batch:

1. Carvacrol of Origanum syriacum essential oil, 0.106%, 106g/100 liters;

2. Carvacrol of *Origanum ehrenbergii* essential oil, 0.076%, 76 g/100 liters;
3. Flavonoids of *Calendula officinalis* leaf's water extract, 0.045%, 45 g/100 liters;
4. Sesquiterpenes of *Matricaria chamomilla* flower's water extract, 0.076%, 76 g/100 liters;
5. Phenols of *Malva sylvestris* leaf's water extract, 0.038%, 38 g/100 liters;
6. Phenols of *Salvia libonitica* leaf's water extract, 0.056%, 56 g/100 liters;
7. Glycerin (99% grade), 6.8%, 6.8 kg/100 liters;
8. Polyoxyethylene sorbitan, 1.6%, 1.6 kg/100 liters; and
9. Sodium bicarbonate, 1.0%, 1.0 kg/100 liters.

A total weight of 98 kg of water extracts from the four herbs, *Calendula officinalis, Matricaria chamomilla, Malva sylvestris,* and *Salvia libonitica,* was added to 6.8 kg of glycerin and 1.0 kg of sodium bicarbonate, and mixed in a sterile container, forming preparation 'A'. In a second container, 200 g of essential oil of each of *Origanum syriacum* and *Origanum ehrenbergii* were added to 1.6 kg of polyoxyethylene sorbitan, and mixed well to form preparation 'B'. Preparation 'B' was added slowly to preparation 'A' while mixing gently. Sterile water was added to the resulting mixture from 'A' and 'B' to reach to a volume of 100 liters. The composition was stirred continuously and the pH was adjusted to 4.75 by the addition of acid or base, depending on the reading of the pH meter.

EXAMPLE 2

In Vitro Trials with Trichomonas Vaginalis

Fresh isolates of *Trichomonas vaginalis* were collected from 30-38 years old women. The procedure of vaginal smearing and reconstituting medium of the collected specimens were performed according to the procedure in Meingassner and Thumer, Antimicrobial agents and Chemotherapy, Vol 15, pp 254-257,1979, incorporated herein by reference in its entirety. Each isolate was adjusted to a viable count of 5,000 cells/ml, using a hemocytometer. A reconstituting diluent, Diamond's TYM supplemented with 10% horse serum, was used. The isolates were tested with the composition and a commonly used drug, metranidazole.

The composition was added to triplicate wells of a microtiter plate and was in contact with equal volume of the adjusted count of each of the twenty isolates for 48 hrs at 37° C. and. in the presence of oxygen. The number of cells in each well was 500 cells/100 µL of medium. The cells were contacted with 100 µL of the composition. Metranidazole was included as a reference at a concentration of 25 µg/ml. Metranidazole (100 µL) was also kept in contact with 500 cells/100 µL of the 20 isolates of *Trichomonas vaginalis* in the presence of oxygen for 48 hours at 37° C. Control triplicate wells were included in which the *Trichomonas vaginalis* cells of each of the 20 isolates were put in contact with equal volume of Diamond's TYM supplemented with 10% horse serum. The motility of flagella of the cells was observed after 48 hrs under an inverted-phase contrast microscope. The percentage of cells losing flagellar motility was determined. Results were presented in Table 1. Both the composition and the reference, metranidazole, resulted in a similar level of inactivation of flagellar motility of the *Trichomonas vaginalis* cells (P>0.05). The level of inactivation was significantly different than what was observed in the control cells that were deprived of any anti-protozoal substance (P<0.05).

TABLE 1

In vitro susceptibility of the 20 isolates of *Trichomonas vaginalis* to the composition and metranidazole

| *Trichomonas vaginalis* isolates | Mean % cells with motility after 48 hrs of aerobic contact with | | |
|---|---|---|---|
| | Douche[1] | Metranidazole[2] | Controls[3] |
| 1 | 12.0 | 4.0 | 80.5 |
| 2 | 9.2 | 0.0 | 85.4 |
| 3 | 14.4 | 1.5 | 93.6 |
| 4 | 8.4 | 5.4 | 78.8 |
| 5 | 9.2 | 7.4 | 90.7 |
| 6 | 12.5 | 0.0 | 87.7 |
| 7 | 13.2 | 9.3 | 93.7 |
| 8 | 7.6 | 5.6 | 88.2 |
| 9 | 10.3 | 8.4 | 79.4 |
| 10 | 4.7 | 10.4 | 94.7 |
| 11 | 9.3 | 0.0 | 97.0 |
| 12 | 5.6 | 4.2 | 87.4 |
| 13 | 10.4 | 0.0 | 89.2 |
| 14 | 11.3 | 6.7 | 92.4 |
| 15 | 9.5 | 8.5 | 88.7 |
| 16 | 8.3 | 11.4 | 94.3 |
| 17 | 10.3 | 7.4 | 96.2 |
| 18 | 9.7 | 8.2 | 87.9 |
| 19 | 10.4 | 9.7 | 95.3 |
| 20 | 1.2.3 | 1.2 | 87.7 |
| Mean of Means | $9.9^a$ | $5.5^a$ | $89.4^b$ |

[1]The composition specified in Example 1
[2]Metranidazole used at a concentration of 25 µg/ml
[3]Controls are isolates deprived of any anti-protozoa substance
[a,b]Mean of means followed by different alphabet superscripts are significantly different at $P < 0.05$.

EXAMPLE 3

In Vitro Trials with *Gardnerella Vaginalis* and *Candida Albicans*

Twenty isolates of each of *Gardnerella vaginalis* and *Candida albicans* were collected from human vaginosis cases. The two groups were grown respectively on brain-heart infusion supplemented with 5% human serum and Sabouraud dextrose broth until their turbidity matched McFarland Tube 2 of barium chloride (Okwoli et al., West Africa Journal of Medicine, Vol 21, pp 244-247, 2002; Saigal at al., Contemporary Clinical Dentistry, Vol 2, pp 188-193, 2011; and Bauer et al., American Journal of Clinical Pathology, Vol 36, pp 493-496, 1966), each incorporated herein by reference in their entirely). The disc diffusion method was used. For *Gardnerella vaginalis,* the Mueller-Hinton agar supplemented with 5% human serum medium was used. For *Candida albicans,* Mueller-Hinton agar supplemented with 2% glucose and 0.5 mcg/ml of methylene blue dye was used (Kamat et al., Indian Journal of Urology, Vol 25, pp 76-80, 2009, incorporated herein by reference in its entirety).

Example 3 shows the in vitro susceptibility of *Gardnerella vaginalis* and *Candida albicans* to the composition in comparison to commonly used chlorhexidine (0.2%)-based douche.

Blank discs overlaid on the agar were loaded with 20 mcl/disc of the composition. For *Trichomonas vaginalis,* reference disks contained 5 mcg of metronidazole/disc. For *Candida albicans,* the reference disks contained amphotericin B (20 mcg/disc). *Trichomonas vaginalis* and *Candida albicans* were also treated with 20 mcl/disc of chlorohexidine(0.2%)-based vaginal douche. The discs were incubated aerobically for 48 hrs at 35° C., the diameter of the discs inhibition zones were measured in millimeter, and interpreted by using the chart provided by Hudzicki, American Society for Microbiology, www.asm.org.2013, incorporated herein by reference in its entirety. The susceptibility of the 20 isolates of each of the two organisms is presented in Table 2. Only one of the 20 isolates of *Gardnerella vaginalis* was resistant to the reference disc of metronidazole, while 6 out of 20 isolates of *Candida albicans* were resistant to amphotericin B (20 mcg).

The percentages of *Gardnerella vaginalis* and *Candida albicans* isolates that were sensitive to discs loaded each, with 20 μL of the composition were significantly higher for the same isolates' sensitivity to loaded discs with same volume of 20 μL of chlorhexidine (0.2%)-based vaginal douche (P<0.05).

TABLE 2

In vitro susceptibility of *Gardnerella vaginalis* and *Candida albicans* to the composition in comparison to commonly used chlorhexidine (0.2%)-based douche

| Microorganism | No. tested isolates | Vaginal douche | % Susceptibility[1] | | |
|---|---|---|---|---|---|
| | | | % R | % I | % S |
| G. vaginalis | 20 | Composition | 0.0 | 10.0 | 90.0[a] |
| | | Chlorhexidine-based | 30.0 | 30.0 | 40.0[b] |
| C. albicans | 20 | Composition | 0.0 | 0.0 | 100.0[a] |
| | | Chlorhexidine-based | 60.0 | 10.0 | 30.0[b] |

[1]R = resistant, I = Intermediate, S = Sensitive; [a,b]%S in a column followed by different alphabet superscripts are significantly different (P < 0.05)

EXAMPLE 4

In Vivo Trials with *Trichomonas Vaginalis*, *Gardnerella vaginalis*, and *Candida Albicans*

In the trials, a mature female mice model was used to study the effect of the composition versus a chlorhexidine (0.2%)-based vaginal douche on the treatment of mice vaginal infection and associated inflammation by each of *Trichomonas vaginalis Gardnerella vaginalis*, and *Candida albicans*. The experimental design included 11 treatment groups, with 10 mature female mice per group. The mice were 12 weeks-old. Each mouse was injected with 0.5 mcg of estradiol valerate/0.5 ml intra-peritoneally on three occasions, with 2 days between each injection. Immediately after receiving the 3$^{rd}$ injection, the vagina of the mice in treatment groups 1 to 3 (T1-T3) were infected with *Trichomonas vaginalis, Gardnerella vaginalis* and *Candida albicans*, respectively, with 10$^4$ cells/50 μl/vagina. The same procedure was respectively administered to the mice in T4-T6, and to the mice in T7-T9. The mice in T1-T3 were subjected to a daily vaginal wash, in the morning and evening, with 100 μl/mouse of the composition between the 4$^{th}$ and 7$^{th}$ day post infection. The mice in. T4-T6 were treated similarly but with the chlorhexidine (0.2%)-based douche. The mice in T7-T9 were not treated with any vaginal douche, while the non-infected mouse in T10 and T11 were respectively treated with the composition and the chlorhexidine-based douche. Mucosal inflammation was recorded for each mouse at 1, 3, and 5 days post the end of vaginal washing. Microscopic examination of vaginal smears of mice infected with *Trichomonas vaginalis* and in non-infected mice of T10 and T11 were done at 1, 3, and 5 days post the end of vaginal washing. Fifty microliter loops were used to scrap vaginal mucosa of each mouse that was infected with *Gardnerella vaginalis* and *Candida albicans,* and the control mice of T10 and T11.

The media used for culturing *Gardnerella vaginalis* and *Candida albicans* were Mueller-Hinton Agar supplemented with 5% human serum medium and Mueller-Hinton Agar suppleirrented with 2% glucose and 0.5 mcg/ml of methylene blue dye, respectively. The percentages of mice in each treatment group cleared of vagina infection and the percentages of mice which developed vaginal inflammation, at the three sampling times, are reported in Table 3. The data shows that the composition is effective in clearing the vaginal infection and reducing the inflammation frequency compared to the chlorhexidine-based douche. The recovery from the infection can occur either in the presence or the absence of the inflammation.

TABLE 3

Effect of the composition versus a commonly used chlorhexidine (0.2%)-based vaginal douche on percentages of mice with vaginal inflammation and percentages with clearance of mice vaginal infection by each of *Trichomons vaginalis, Gardnerella vaginalis*, and *Candida albicans*

| | | | % clearance of vaginal Infection/% vaginal inflammation at different days post the end of douche treatment | | |
|---|---|---|---|---|---|
| Treatments | Vaginal infection By | Vaginal douche | D1 | D3 | D4 |
| T1 | *T. vaginalis* | The composition | 90/8 | 90/10 | 90/10 |
| T2 | *G. vaginalis.* | The composition | 100/0 | 100/0 | 100/0 |
| T3 | *C. albicans* | The composition | 100/0 | 100/0 | 100/0 |
| T4 | *T. vaginalis* | Chlorhexidine-based douche | 20/60 | 30/70 | 30/70 |
| T5 | *G. vaginalis* | Chlorhexidine-based douche | 40/40 | 40/40 | 40/50 |
| T6 | *C albicans* | Chlorhexidine-based douche | 30/50 | 40/50 | 40/60 |
| T7 | *T. vaginalis* | None | 10/90 | 10/90 | 10/90 |
| T8 | *C. vaginalis* | None | 0/100 | 0/100 | 0/100 |
| T9 | *C. albicans* | None | 0/100 | 0/100 | 0/100 |
| T10 | None | The composition | NI[a] | NI | NI |
| T11 | None | Chlorhexidine-based douche | NI | NI | NI |

[a]NI = No infection by either of *Trichomonas vaginalis, Gardnerella vaginalis*, or *Candida albicans*

EXAMPLE 5

Reestablishing *Vaginal Lactobacilli* after the administration of the composition Example 5 is related to safety and ability of beneficial *vaginal lactobacilli* to reestablish after application of the composition versus the application of chlorhexidine-based vaginal douche in mature women.

Twenty 30-38 years old women with no history of vaginosis were divided evenly into two treatment groups, T1 and T2. The Vaginal mucosal irritation of all included subjects was recorded and the subjects' vaginal smears were cultured on specific medium for *lactobacilli* count before application of any douche, thus serving as a control (MacFaddin, Media for isolation, cultivation, identification, maintenance of medical bacteria (Book), Baltimore, London, Williams and Wilkins, ISBN: 0683053167, 1985, incorporated herein by reference in its entirety). Women in T1 washed with the composition, in the morning and evening, using 100 /ml/wash/woman and a contact time of 5 minutes for 4 days.

Women in T2 washed with the chlorhexidine-based douche using the same volume, frequency, contact time, and duration as used by the women in T1. The presence of vaginal mucosal irritation that could have been caused by either of the two douches was recorded at the end of the 4$^{th}$ day of washing. Vaginal smears were taken at two weeks post the end of washing to study the reestablishment of beneficial *lactobacilli*. Results are shown in Table 4.

There was a tendency for women who washed with the chlorhexidine-based douche to show vaginal irritation by the end of the wash regimen. On the contrary, women who washed with the composition did not report any vagina irritation (P>0.05). This observation reflected the safety of the composition. In addition, there was a significant rapid reestablishment (i.e., two weeks after the end of the administration) in *vaginal lactobacilli* count in women who washed with the composition, compared to the women who washed with the chlorhexidine-based douche (P<0.05). This observation indicated a harmless impact of the composition on the beneficial *vaginal lactobacilli*.

While not being bound by theory, it is believed that the restoration of the *lactobacilli* count will indirectly contribute to the maintenance of the low pH environment that is essential for the physiologic homeostasis of the vagina.

TABLE 4

Safety and ability in reestablishing beneficial vaginal lactobacilli after application of the composition versus the application of chlorhexidine-based douche in women

| Treatment[1] | Vaginal Douche[2] | % women with Irritation in vagina | | Mean Lactobacilli count/g | |
|---|---|---|---|---|---|
| | | Before Wash | End of wash | Before Wash | end of Wash |
| T1 | Developed Douche | 0.0 | 0.0$^a$ | $(3.5 \times 10^6)^a$ | $(3.1 \times 10^6)^a$ |
| T2 | Chlorhexidine-based | 0.0 | 30.0$^a$ | $(3.2 \times 10^6)^a$ | $(1.6 \times 10^5)^b$ |

[1]Ten women with no history of vaginosis were included in each treatment
[2]The vaginal douches were applied for a period of 4 days, morning and evening, using a volume of 100 cc./wash/woman

The invention claimed is:

1. A composition, comprising:
   0.01-10 g/L of an essential oil extracted from *Origanum syriacum* and *Origanum ehrenbergii*;
   100-500 g/L of an aqueous extract of *Calendula officinalis*;
   100-500 g/L of an aqueous extract of *Matricaria chamomilla*;
   100-500 g/L of an aqueous extract of *Malva sylvestris*;
   100-500 g/L of an aqueous extract of *Salvia libanotica*; and
   1-100 g/L of polyoxyethylene sorbitan, each based on a total volume of the composition,
   wherein a pH of the composition is in a range of 4-5.5, and the composition is substantially free of a $C_1$-$C_6$ aliphatic alcohol, the composition is substantially free of an aromatic alcohol, and the composition is substantially free of a $C_3$-$C_{25}$ diol.

2. The composition of claim 1, wherein the aqueous extract of *Calendula officinalis* is sourced from a leaf.

3. The composition of claim 1, wherein the aqueous extract of *Matricaria chamomilla* is sourced from a flower.

4. The composition of claim 1, wherein the aqueous extract of *Malva sylvestris* is sourced from a leaf.

5. The composition of claim 1, wherein the aqueous extract of *Salvia libanotica* is sourced from a leaf.

6. The composition of claim 1, comprising:
   1-7 g/L of the essential oil extracted from *Origanum syriacum* and *Origanum ehrenbergii*;
   200-300 g/L of the aqueous extract of *Calendula officinalis*;
   200-300 g/L of the aqueous extract of *Matricaria chamomilla*;
   200-300 g/L of the aqueous extract of *Malva sylvestris*;
   200-300 g/L of the aqueous extract of *Salvia libanotica*; and
   15-30 g/L of polyoxyethylene sorbitan, each based on the total volume of the composition.

7. A method for at least one of treating a vaginal infection, treating a vaginal inflammation, and reestablishing vaginal *lactobacilli* in a subject in need thereof, the method comprising:
   administering an effective amount of the composition of claim 1 at least once daily to the subject in need thereof, wherein a source of the vaginal infection and/or the vaginal inflammation is at least one selected from the group consisting of *Trichomonas vaginalis*, *Gardnerella vaginalis*, and *Candida albicans*.

8. The method of claim 7, wherein the effective amount is in a range of 1-10 ml/kg body weight.

9. The method of claim 7, wherein the method reestablishes the vaginal *lactobacilli* and the subject is administered with the effective amount of the composition for one to 30 consecutive days, and the method further comprises measuring the vaginal *lactobacilli* count before the administering and/or measuring the vaginal *lactobacilli* count at least one week after the end of the administering.

10. A personal care product comprising the composition of claim 1.

11. The composition of claim 1, wherein:
   the aqueous extract of *Calendula officinalis* is sourced from a leaf;
   the aqueous extract of *Matricaria chamomilla* is sourced from a flower;
   the aqueous extract of *Malva sylvestris* is sourced from a leaf; and
   the aqueous extract of *Salvia libanotica* is sourced from a leaf.

12. The method of claim 7, wherein the composition is administered as a vaginal wash.

* * * * *